US007943124B2

(12) United States Patent
Moro et al.

(10) Patent No.: US 7,943,124 B2
(45) Date of Patent: May 17, 2011

(54) COMPOSITION FOR IMMUNOSTIMULATION

(75) Inventors: Itaru Moro, Tokyo (JP); Takashi Iwase, Tokyo (JP); Kuniyasu Ochiai, Tokyo (JP); Masako Yajima, Kanagawa (JP); Masaki Terahara, Kanagawa (JP); Yoshitaka Nakamura, Kanagawa (JP); Mamoru Totsuka, Tokyo (JP); Kiyoshi Yamada, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 462 days.

(21) Appl. No.: 11/815,136

(22) PCT Filed: Feb. 1, 2006

(86) PCT No.: PCT/JP2006/301661
§ 371 (c)(1),
(2), (4) Date: Jan. 4, 2008

(87) PCT Pub. No.: WO2006/087913
PCT Pub. Date: Aug. 24, 2006

(65) Prior Publication Data
US 2009/0142374 A1 Jun. 4, 2009

(30) Foreign Application Priority Data

Feb. 2, 2005 (JP) ................................. 2005-026631
Sep. 5, 2005 (JP) ................................. 2005-256835

(51) Int. Cl.
*A01N 63/00* (2006.01)
*A61K 39/00* (2006.01)
*A61K 39/02* (2006.01)
*A61K 38/00* (2006.01)
*C12P 1/00* (2006.01)

(52) U.S. Cl. .................... 424/93.1; 424/93.4; 424/184.1; 424/234.1; 435/41; 530/300

(58) Field of Classification Search ........................ None
See application file for complete search history.

(56) References Cited

U.S. PATENT DOCUMENTS

| 5,192,685 A | 3/1993 | Yasui et al. |
| 2004/0110270 A1 | 6/2004 | Dennin et al. |

FOREIGN PATENT DOCUMENTS

| EP | 0640349 | | 3/1995 |
| EP | 0640 349 A1 * | | 9/1995 |
| JP | 2-280059 | | 11/1990 |
| JP | 4-342533 | | 11/1992 |
| JP | 7-069907 | | 3/1995 |
| JP | 7-106142 | | 11/1995 |
| JP | 2002-255853 | | 9/2002 |
| JP | 2002-255853 A * | | 9/2002 |
| JP | 2003-201239 | | 7/2003 |
| JP | 2004-262773 | | 9/2004 |
| JP | 7-061934 | | 3/2005 |
| JP | 2005-089388 | | 4/2005 |

OTHER PUBLICATIONS

Park et al (Cell Immunology, 2002, 219,(1) p. 22-27).*
Manufacturer's Product Description for MTT Cell Viability Assay Kit, Biotium Inc.
Partial English—language Translation of JP 2002-255853A (Eiko et al).
Perrier et al., "Glycans on Secretory Component Participate in Innate Protection against Mucosal Pathogens" *Journal of Biological Chemistry* 281(20):14280-14287, 2006.
Gang MA et al., "Study on Bifidobacterial Milk," Food & Fermentation Industries, No. 1, pp. 13-18, including an English language Abstract, 1992.
Chinese Office Action issued Mar. 15, 2010 in connection with patent family member Chinese Patent Application No. 200680010464.4, along with a partial English language translation thereof.
Park et al., Encapsulated *Bifidobacterium bifidum* potentiates intestinal IgA production, *Cell. Immunol.*, vol. 219, No. 1, pp. 22-27 (2002).
Qiao et al., Immune Responses in Rhesus Rotavirus-Challenged Balb/c Mice Treated with Bifidobacteria and Prebiotic Supplements, *Pediatric Research*, vol. 51, No. 6, pp. 750-755 (2002).
English Language Abstract of JP 2002-255853, Sep. 11, 2002.
English Language Abstract of JP 2005-089388, Apr. 7, 2005.
English Language Abstract of JP 7-061934, Mar. 7, 1995.
English Language Abstract of JP 4-342533, Nov. 30, 1992.
English Language Abstract of JP 2-280059, Nov. 16, 1990.
Hosono et al., Men'ekikei to Sogosayo suru Chonai Saikin (Probiotics), Allergology, vol. 18, No. 6, pp. 483-489 (2004), along with a partial English-language translation thereof.
Ko et al., *Bifidobacterium bifidum* Exhibits a Lipopolysaccharide-Like Mitogenic Activity for Murine B Lymphocytes, *J. Dairy Science*, vol. 82, No. 9, pp. 1869-1876 (1999).
English Language Abstract of JP 2004-262773, Sep. 24, 2004.
English Language Abstract of JP 2003-201239, Jul. 18, 2003.
English Language Abstract of patent family member JP 2-280059, Nov. 16, 1990.
English Language Abstract of JP 7-069907, Mar. 14, 1995.
Takahashi et al., Effects of Orally Ingested *Bifidobacterium longum* on the Mucosal IgA Response of Mice to Dietary Antigens, *Biosci. Biotechnol. Biochem.*, vol. 62, No. 1, pp. 10-15 (1998).
Giugliano et al., Free secretory component and lactoferrin of human milk inhibit the adhesion of enterotoxigenic *Escherichia coli, J. Med. Microbiol.*, vol. 42, pp. 3-9 (1995).
Dallas et al., Binding of *Clostridium difficile* toxin A to human milk secretory component, *J. Med. Microbiol.*, vol. 47, pp. 879-888 (1998).

(Continued)

*Primary Examiner* — Vanessa L. Ford
(74) *Attorney, Agent, or Firm* — Greenblum & Bernstein, P.L.C.

(57) ABSTRACT

The present invention relates to a composition for immunostimulation useful for promoting IgA and secretory component productions in mucosal tissues, comprising, alone or in combination, a cell of *bifidobacterium* belonging to *Bifidobacterium bifidum* or a processed product thereof, wherein the *bifidobacterium* has an activity to stimulate secretory component production and a high activity to stimulate IgA production, for example, it is a *Bifidobacterium bifidum* OLB 6377 strain or *Bifidobacterium bifidum* OLB 6378 strain.

7 Claims, 6 Drawing Sheets

OTHER PUBLICATIONS

Johansen et al., Absence of Epithelial Immunoglobulin A Transport, with Increased Mucosal Leakiness, in Polymeric Immunoglobulin Receptor/Secretory Component—deficient Mice, *J. Exp. Med.*, vol. 190, No. 7, pp. 915-921 (1999).

Ha et al., Depression in the Quantity of Intestinal Secretory IgA and in the Expression of the Polymeric Immunoglobulin Receptor in Caloric Deficiency of the Weanling Mouse, *Lab. Invest.*, vol. 78, No. 10, pp. 1255-1266 (1998).

Suzuki et al., Rapid Preparation of Functional Murine Payer's Patch Cells, *Bifidobacteria Microflora*, vol. 9, No. 2, pp. 87-98 (1990).

Blanch et al., Cutting Edge: Coordinate Regulation of IFN Regulatory Factor-1 and the Polymeric Ig Receptor by Proinflammatory Cytokines, *J. Immunol.*, vol. 162, pp. 1232-1235 (1999).

\* cited by examiner

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggcaatgac aacatgggg                                                 19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
atgtcagctt cctccttgg                                               19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaacgggaa gctcactgg                                               19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccaccaccc tgttgctgta                                              20
```

COMPOSITION FOR IMMUNOSTIMULATION

TECHNICAL FIELD

The present invention relates to a composition for immunostimulation comprising a bifidobacterium belonging to Bifidobacterium bifidum and/or a processed product of the bifidobacterium. The present invention also relates to a food or drink product and a pharmaceutical composition useful for immunostimulation comprising the same.

BACKGROUND ART

The mucosal surface of the bronchi, gastrointestinal tract, urogenital system, or the like has a strong mucosal immune system in which secretory IgA play a major role in protecting the organism against microorganisms such as bacteria and viruses, and many foreign antigens including dietary proteins and the like. The secretory IgA, unlike IgA in serum, exists in the form of a J-chain-containing dimeric IgA (2IgA-J) bound with a secretory component (SC; or secretory piece) (2IgA-J-SC) and is contained in large amounts in saliva, tears, nasal secretion, breast milk, and secretions from the bronchi, intestines, or the like. Lymphoid tissues in such mucosal surface are called mucosa-associated lymphoid tissues and play a central role in the induction of IgA production. In mucosal immunity, B cells activated by antigenic stimulation in Peyer's patch, a representative intestinal mucosa-associated lymphoid tissue, or the like are redistributed in the mucosal surfaces of not only the intestines but also the exocrine glands, bronchi, and urogenital system through systemic circulation and then differentiated into plasma cells, IgA-producing cells to produce dimeric IgA. The produced dimeric IgA is further converted into secretory IgA through binding with a secretory component produced in mucosal epithelial cells, and secreted from within the mucosa to lumens or the outside of the organism. The secretory component has been known to be essential for secreting dimeric IgA to lumens or the outside of the organism.

Thus, a food component or composition that induces and establishes dimeric IgA production and secretory component production in the mucosa of the bronchi, gastrointestinal tracts, urogenital system, or the like can be expected to increase the amount of secretory IgA production or secretory IgA secretion from the mucosa to lumens or the outside of the organism and thereby enhance the biophylaxis capacity. The enhancement of such a biophylaxis capacity of mucosal immunity is particularly useful for the prevention of pathogen invasion into bodies, the prevention of occurrence of food allergy, and so on.

The present inventors have found, for example, fructo-oligosaccharide and a composition thereof as substances promoting secretory IgA production (Patent Document 1). This fructo-oligosaccharide is one of the few food components that have been reported about their influence on secretory component production. On the other hand, bifidobacteria Bifidobacterium longum and Bifidobacterium breve have heretofore been known to stimulate IgA production in Peyer's patch cells (Patent Document 2). Moreover, the present inventors have previously found that Bifidobacterium longum OLB 6001 strain separated from human adult feces has an IgA production-stimulating ability (Non-Patent Document 1). This bifidobacterium Bifidobacterium longum OLB 6001 strain is identical to Bifidobacterium longum No. 7 (accession No. FERM P-13610) reported by the group of the present inventors (Patent Document 3). However, the further emergence of a composition for immunostimulation having higher immunostimulating effect, which exceeds even those of these bifidobacteria, is still demanded.

Patent Document 1: JP Patent Publication (Kokai) No. 2003-201239A (2003)
Patent Document 2: JP Patent Publication (Kokoku) No. 7-106142B (1995)
Patent Document 3: JP Patent Publication (Kokai) No. 7-69907A (1995)
Non-Patent Document 1: Takahashi T., Nakagawa E., Nara T., Yajima T. and Kuwata T., Biosci. Biotechnol. Biochem., 62 (1), (1998) p. 10-15

DISCLOSURE OF THE INVENTION

An object of the present invention is to provide a composition for immunostimulation and a food or drink product and a pharmaceutical composition useful for immunostimulation.

The present inventors have conducted studies for attaining the object and have consequently completed the present invention by successfully obtaining, from among bifidobacterium strains belonging to Bifidobacterium bifidum, plural strains useful for immunostimulation that can promote both secretory component production and dimeric IgA production in the intestinal mucosal system. Specifically, the present invention encompasses the following.

[1] A composition for immunostimulation comprising a bifidobacterium belonging to Bifidobacterium bifidum and/or a processed product of the bifidobacterium, wherein said bifidobacterium has an ability to stimulate secretory component production so as to increase the amount of secretory component production in an intestinal epithelial cell by at least 1.2 times.

[2] The composition for immunostimulation of [1], wherein said bifidobacterium further has an ability to stimulate IgA production so as to increase the amount of IgA production per $5 \times 10^5$ Peyer's patch cells in the presence of an anti-CD3 antibody to at least 10 μg/ml.

[3] The composition for immunostimulation of [1] or [2], wherein said bifidobacterium is Bifidobacterium bifidum OLB 6377 strain (accession No. NITE BP-30) or Bifidobacterium bifidum OLB 6378 strain (accession No. NITE BP-31).

[4] The composition for immunostimulation of any of [1] to [3], wherein said processed product of the bifidobacterium is at least one selected from the group consisting of suspensions, cultures, culture supernatants, fermented products, heat-treated products, cell lysates, concentrates, pastes, dried products, and diluted products of the bifidobacterium.

[5] A food or drink product comprising the composition for immunostimulation of any of [1] to [4].

[6] The food or drink product of [5], wherein the food or drink product is selected from the group consisting of baby foods, infant foods, foods for lactating women, foods for elderly persons, foods for sick persons, foods with health claims, supplements, fermented milks, and lactic acid bacteria beverages.

[7] A pharmaceutical composition comprising the composition for immunostimulation of any of [1] to [4].

[8] Use of Bifidobacterium bifidum OLB 6377 strain (accession No. NITE BP-30) or Bifidobacterium bifidum OLB 6378 strain (accession No. NITE BP-31) for preparation of a food or drink product or a pharmaceutical composition for immunostimulation.

[9] A *bifidobacterium* of the following (a) or (b):
   (a) *Bifidobacterium bifidum* OLB 6377 strain (accession No. NITE BP-30); and
   (b) *Bifidobacterium bifidum* OLB 6378 strain (accession No. NITE BP-31).

EFFECTS OF THE INVENTION

The composition for immunostimulation of the present invention can promote secretory component production in epithelial cells and can considerably strongly induce IgA production in Peyer's patch cells, compared with conventional bifidobacteria such as *Bifidobacterium longum* and *Bifidobacterium breve*, which have been reported to have immunostimulating effect. Therefore, the composition for immunostimulation of the present invention is very useful, particularly, for the activation of mucosal immunity. Furthermore, the food or drink product and the pharmaceutical composition of the present invention comprising the composition for immunostimulation as an active ingredient have less potential for side effects, because the composition for immunostimulation is derived from bifidobacteria ingested as food by humans for a long time. The use of the *Bifidobacterium bifidum* OLB 6377 strain (accession No. NITE BP-30) or *Bifidobacterium bifidum* OLB 6378 strain (accession No. NITE BP-31) of the present invention can produce the composition for immunostimulation that can promote secretory component production and can induce IgA production several times as strongly as conventional bifidobacteria.

The Japanese patent Application Nos. 2005-026631 and 2005-256835 of which the present application claims the priority are described herein.

BEST MODE FOR CARRYING OUT THE INVENTION

Hereinafter, the present invention will be described in detail.
1. *Bifidobacterium* for Use and Screening Thereof.

In the present invention, a *bifidobacterium* belonging to *Bifidobacterium bifidum* which have an ability to stimulate secretory component production and a high ability to stimulate IgA production is used to prepare a composition for immunostimulation.

"*Bifidobacterium bifidum*" to which the *bifidobacterium* for use in the present invention belongs is one species of the genus *Bifidobacterium*. In the present invention, the *bifidobacterium* classified into *Bifidobacterium bifidum* can be identified according to usual taxonomic criterion, or can also be identified by a molecular biological approach frequently used in recent years, for example, a method using a DNA probe specific to *Bifidobacterium bifidum* (Intestinal Flora Symposium 8 "Molecular Ecological Detection and Identification of Intestinal Flora"), or based on DNA homologies to standard strains.

In the present invention, the "ability to stimulate secretory component production" refers to a capacity to promote secretory component secretion from mucosal epithelial cells, e.g., but not limited to, intestinal epithelial cells. The ability to stimulate secretory component production can be represented, for example, as a rate of increase in a concentration of secretory component or as a relative amount of secretory component which is secreted from mucosal epithelial cells that have been contacted with the *bifidobacterium* or a processed product of the *bifidobacterium* compared to that of a control experiment group without use of the *bifidobacterium* or the like. More specifically, the "ability to stimulate secretory component production" of the *bifidobacterium* of the present invention corresponds to an ability to increase the amount of a secretory component production in an intestinal epithelial cell by at least 1.2 times, preferably 1.4 times or more, generally 1.2 to 10 times, typically 1.2 to 3 times.

It is preferred that the *bifidobacterium* for use in the present invention is selected, from among bifidobacteria belonging to *Bifidobacterium bifidum*, as a strain that can increase the amount of a secretory component production in an intestinal epithelial cell by at least 1.2 times. The amount of a secretory component production can be determined in vitro, for example, as described in Examples described below.

Such a *bifidobacterium* can be selected on the basis of, for example, but not limited to, an assay method described in Examples of the present specification. In brief, a *bifidobacterium* belonging to *Bifidobacterium bifidum* is first cultured in an anaerobic EG medium prepared by using lactose instead of glucose. The bacterial cells in the resulting cultured product are washed and subsequently subjected to heat treatment and ultrasonic disruption to obtain a bacterial cell lysate. This bacterial cell lysate is added to a medium seeded with a human intestinal epithelial cell-derived cell line (e.g., HT-29 cells), and cultured, preferably, at 37° C. for 48 hours. Then, a secretory component concentration in the culture supernatant thereof is measured. Alternatively, a suspension of cultured bacterial cells in PBS(−) may be added directly instead of the bacterial cell lysate to the medium. Further, a control experiment is conducted and a secretory component concentration in the culture supernatant is determined by the same experimental procedure except that PBS(−) (i.e., Dulbecco's Phosphate Buffered Saline without Ca and Mg ions) is used instead of the bacterial cell lysate. The secretory component concentration can be measured by an ELISA method. Next, the measurement value of the secretory component concentration obtained in the experimental group is converted into a relative value to the measurement value of the secretory component concentration of the control experiment group defined as 1. The relative value thus obtained can be considered as a level of an increase in the amount of a secretory component production in an intestinal epithelial cell. Specifically, it is preferred that a *bifidobacterium* that shows 1.2 or higher as this relative value is selected. For example, when a relative value obtained by the assay using a certain *bifidobacterium* strain is 1.5, this *bifidobacterium* strain can be considered as having an ability to increase the amount of a secretory component produced from an intestinal epithelial cell by 1.5 times and may be selected as the *bifidobacterium* for use in the present invention. The culture system of this assay method contains no plasma cell (IgA-producing cell). Therefore, in this assay system, a secretory component is secreted alone into the culture supernatant in unbound form with IgA.

The ability to stimulate secretory component production of the *bifidobacterium* for use in the present invention is also supported by the effect providing an increase of a secretory component gene expression level in the intestine. The *bifidobacterium* for use in the present invention can increase a secretory component gene expression level, preferably, by at least 2.0 times. An increase in secretory component gene expression level caused by the *bifidobacterium* of the present invention can specifically be confirmed as an increase in the percentage of mRNA (e.g., accession No. BC013556; in International Nucleotide Sequence Database) compared to the total RNA level, expressed from pIgR gene (polymeric immunoglobulin receptor gene; Gene ID: 18703; Shimada S. et al., J. Immunol. 1999; 163 (10): 5367-73), i.e., secretory component gene, in the small intestine or large intestine. A level of mRNA derived from pIgR gene can be determined on the basis of the amount of an amplification product detected, for example, by preparing cDNA via reverse transcription PCR using total RNA extracted from the tissue of the small intestine (e.g., ileum or jejunum) or large intestine (e.g., proximal large intestine) as a template and an oligo dT primer, and then performing real-time PCR using the obtained cDNA as a template and a primer pair specific to the pIgR gene. The intestinal tissue to be subjected to the measurement of a pIgR gene expression level may be organ-cultured to uniformize the measurement conditions. It is also preferred that GAPDH gene, β-actin gene, or the like, should be utilized as an internal standard for real-time PCR. These genes can be obtained as commercially available hybridization probes (Applied Biosystems, Stratagene, etc.), and employed preferably as internal standards.

The present invention also encompasses such a method of selecting a *bifidobacterium*, such as a method for screening a *bifidobacterium* having advantageous functionality including high immunostimulating effect by determining a level of enhancement in the amount of a secretory component produced from a mucosal epithelial cell.

It is also preferred that the *bifidobacterium* for use in the present invention is a *bifidobacterium* that can increase a secretory component gene expression level as described above and can further increase an expression level of interferon regulatory factor 1 gene (IRF-1 gene) in the intestine. Preferably, the *bifidobacterium* for use in the present invention can increase IRF-1 gene expression level in an intestinal tissue by at least 1.5 times. An increase in IRF-1 gene expression level caused by the *bifidobacterium* of the present invention can specifically be confirmed as an increase in the percentage of mRNA (e.g., accession No. NM008390; International Nucleotide Sequence Database) compared to the total RNA level, expressed from IRF-1 gene (interferon regulatory factor 1; Gene ID: 16362) in the small intestine or large intestine. A level of mRNA derived from IRF-1 gene can be determined from the amount of an amplification product detected, for example, by preparing cDNA via reverse transcription PCR using total RNA extracted from the tissue of the small intestine (e.g., ileum or jejunum) or large intestine (e.g., proximal large intestine) as a template and an oligo dT primer, and then performing real-time PCR using the obtained cDNA as a template and a primer pair specific to the IRF-1 gene. Furthermore, a change in a level of mRNA derived from IRF-1 gene can also be analyzed by DNA microarray method using cRNA prepared by using total RNA as a template. The intestinal tissue to be subjected to the measurement of an IRF-1 gene expression level may be organ-cultured to uniformize the measurement conditions. It can be considered that such an increase in IRF-1 gene expression level probably results in an increase in the amount of a secretory component production via an intracellular signaling pathway in the intestinal tissue to which the *bifidobacterium* or the processed product thereof according to the present invention has been administered, although the present invention is not intended to be constrained by such a theory.

On the other hand, in the present invention, the "ability to stimulate IgA production" refers to a capacity to promote IgA secretion from plasma cells present in mucosa-associated lymphoid tissues, e.g., but not limited to, intestinal mucosa. The ability to stimulate IgA production can be represented, for example, as a rate of increase in a concentration of IgA which is secreted from mucosa-associated lymphoid tissues that have been contacted with the *bifidobacterium* or a processed product of the *bifidobacterium* compared to that of a control experiment group obtained without use of the *bifidobacterium* or the like. Alternatively, this ability to stimulate IgA production may be represented by the concentration of IgA produced from IgA-producing cells derived from mucosa-associated lymphoid tissues in a given assay system. The *bifidobacterium* of the present invention has an ability to stimulate IgA production higher than those of conventional bifidobacteria which have been reported to have an ability to stimulate IgA production. More specifically, the "high ability to stimulate IgA production" of the *bifidobacterium* of the present invention corresponds to an ability to increase the amount of IgA production per $5 \times 10^5$ Peyer's patch cells in the presence of an anti-CD3 antibody in an in vitro experiment system to a level of at least 10 µg/ml, generally 10 µg/ml to 100 µg/ml, typically 10 µg/ml to 30 µg/ml.

It is preferred that the *bifidobacterium* for use in the present invention is selected, from among bifidobacteria belonging to *Bifidobacterium bifidum*, as a strain that can increase the amount of IgA production per $5 \times 10^5$ Peyer's patch cells in the presence of an anti-CD3 antibody, for example, in an assay system described below, to at least 10 µg/ml.

The assay for the selection of a *bifidobacterium* on the basis of the amount of IgA produced can be conducted as described below on the basis of, for example, but not limited to, the description of Examples of the present specification. In brief, the *bifidobacterium* belonging to *Bifidobacterium bifidum* is first cultured in an anaerobic EG medium prepared by using lactose instead of glucose. The bacterial cells in the resulting cultured product are washed and then fixed with, for example, 4% formalin-PBS. The fixed bacterial cells are subjected, if necessary, to formalin removal or the like, and then, the concentration of the bacterial solution is adjusted so that the turbidity at 660 nm is set to 1.6. On the other hand, Peyer's patch collected from a mouse is broken up into a medium (e.g., an RPMI-1640 medium containing 2% bovine fetal serum), passed through a 150-gauge sterile stainless steel sieve and washed. Then, the cells are resuspended in a medium to prepare a lymphoid cell population including T and B cells. In the present assay, the lymphoid cell population is used as Peyer's patch cells. Thus, next, the lymphoid cell population is seeded at a density of $5 \times 10^5$ cells/well into a plate coated in advance with an anti-CD3 antibody. To this well, 5 μL of the bacterial solution (turbidity=1.6) described above was added and cultured at 37° C. for 5 days in a carbon dioxide incubator. A culture supernatant is collected by removing the lymphoid cells from the cultured product. An IgA amount in the culture supernatant is measured. This IgA amount in the culture supernatant can be considered as the amount of IgA production per $5 \times 10^5$ Peyer's patch cells in the presence of an anti-CD3 antibody. Specifically, it is preferred that a *bifidobacterium* that shows 10 μg/ml or more as this IgA amount in the culture supernatant is selected. Moreover, a control experiment may be conducted and an IgA amount in the culture supernatant may be measured in the same way as above except that no *bifidobacterium* solution is added. The IgA amount in the culture supernatant of the experimental group can also be converted into a relative value to the IgA amount of the control experiment group defined as 1. The great majority of IgAs measured in the present assay method are probably dimeric IgAs secreted, to the outside of cells, from plasma cells (IgA-producing cells) differentiated in Peyer's patch cells in the presence of an anti-CD3 antibody.

The ability to stimulate IgA production of the *bifidobacterium* for use in the present invention can also be specified by comparing to, as a reference, that of *bifidobacterium* strain *Bifidobacterium longum* OLB 6001 strain (accession No. FERM P-13610) or a *Bifidobacterium breve* strain (accession No. FERM BP-2824) heretofore reported to have a high ability to stimulate IgA production. They are strains that have been deposited with International Patent Organism Depositary, National Institute of Advanced Industrial Science and Technology (Tsukuba Central 6, 1-1-1 Higashi, Tsukuba, Ibaraki, Japan). For example, in the assay method on the basis of the amount of IgA production, a control experiment may be conducted by the same procedure except that the *Bifidobacterium longum* OLB 6001 strain or the *Bifidobacterium breve* strain (accession No. FERM BP-2824) is used instead of the *bifidobacterium* in the experimental group. The IgA amount in the culture supernatant of the experimental group may be converted to a relative value to the IgA amount in the culture supernatant of this control experiment group defined as 1. As a result, the ability to stimulate IgA production of the *bifidobacterium* of the present invention can be also represented as the relative value indicating an ability of the *bifidobacterium* to promote IgA production in Peyer's patch cells in the presence of an anti-CD3 antibody. For example, when the relative value of the IgA amount of a certain *bifidobacterium* strain belonging to *Bifidobacterium bifidum* to the IgA amount in the culture supernatant in the case of using *Bifidobacterium longum* OLB 6001 strain defined as 1 is 3 as a result of the assay, this *bifidobacterium* strain has an ability to stimulate IgA production that can increase the amount of IgA produced in Peyer's patch cells in the presence of an anti-CD3 antibody by 3 times, compared with that of the *Bifidobacterium longum* OLB 6001 strain. The ability to stimulate IgA production of the *bifidobacterium* for use in the present invention has an ability to stimulate IgA production that can increase the amount of IgA produced in Peyer's patch cells in the presence of an anti-CD3 antibody by 2 to 10 times, preferably 2.4 to 5 times, compared with, for example, that of the *Bifidobacterium longum* OLB 6001 strain.

In the present invention, the ability to stimulate secretory component production and the ability to stimulate IgA production of the *bifidobacterium* to be used can also be confirmed by use of the assay methods as described above.

*Bifidobacterium* strains that can be particularly preferably used in the present invention are bifidobacteria *Bifidobacterium bifidum* OLB 6377 and *Bifidobacterium bifidum* OLB 6378 strains that have been separated from infant's feces by the present inventors on their own. Both of these strains have been identified to belong to *Bifidobacterium bifidum* by study using DNA probes specific to the bacterial species. These strains were deposited on Oct. 26, 2004 (original deposition date) with Patent Microorganisms Depositary, National Institute of Technology and Evaluation (2-5-8 Kazusakamatari, Kisarazu, Chiba, Japan) as deposition Nos. NITE P-30 for the *Bifidobacterium bifidum* OLB 6377 strain and NITE P-31 for the *Bifidobacterium bifidum* OLB 6378 strain. These strains were transferred on Jan. 18, 2006 from the original deposition to deposition based on the Budapest Treaty. The deposition Nos of the *Bifidobacterium bifidum* OLB 6377 and *Bifidobacterium bifidum* OLB 6378 strains were changed to NITE BP-30 and NITE BP-31, respectively. Moreover, these strains have been confirmed by the assays to have an ability to stimulate secretory component production, and an ability to stimulate IgA production 2 to 5 times higher than those of conventional bifidobacteria, as described in detail in Examples. Variant strains and so on derived from these strains can also be used preferably in the present invention as long as they have an ability to stimulate secretory component production and a high ability to stimulate IgA production.

A conventional culture medium used in *bifidobacterium* culture can be used for culturing the *bifidobacterium* of the present invention. Specifically, any medium appropriately containing main carbon sources as well as nitrogen sources, inorganic substances, and other nutrients may be used. More excellent growth is obtained in the medium supplemented with a sulfur-containing amino acid such as cysteine, cystine, or methionine. Lactose, glucose, sucrose, fructose, galactose, blackstrap molasses, or the like can be used as a carbon source depending on assimilation capacity of the bacterium to be used. An organic nitrogen-containing substance such as a casein hydrolysate, whey protein hydrolysate, or soybean protein hydrolysate can be used as a nitrogen source. In addition, meat extracts, fish meat extracts, yeast extracts, and the like are used as a growth promoting agent.

The *bifidobacterium* of the present invention can be cultured under anaerobic conditions. A method of culture in a medium aerated in advance with a carbon gas or an approach known in the art such as a method using an anaerobic jar incorporating therein an oxygen scavenger, e.g., AnaeroPack or GasPack, can be applied to the anaerobic culture. In general, a culture temperature is preferably 35 to 40° C. However, other temperature conditions may be used as long as these temperatures allow for bacterial growth. It is preferred that the pH of the medium at the start of culture is kept at 5.0 to 8.0. An appropriate culture time for obtaining a culture to be used for the production of a composition for immunostimulation is usually 10 to 20 hours.

2. Composition for Immunostimulation

In the present invention, a composition comprising the *bifidobacterium* of the present invention can be used as a composition for immunostimulation. A composition comprising a processed product of the *bifidobacterium* of the present invention in addition to or instead of the *bifidobacterium* of the present invention may also be used as a composition for immunostimulation. The composition for immunostimulation of the present invention stimulates (or promotes) secretory component production from mucosal epithelial cells such as intestinal epithelial cells and stimulates (promotes) IgA production at a high level in mucosa-associated lymphoid tissues including Peyer's patch cells.

The addition of the composition for immunostimulation of the present invention in appropriate amounts can impart immunostimulating effect, for example, the suppression of infection with pathogens, to a food or drink product or a pharmaceutical composition. This composition for immunostimulation may be prepared in any form including, but not limited to, liquids, gels, powders, granules, solids, capsules, and tablets.

The *bifidobacterium* of the present invention to be used in the composition for immunostimulation of the present invention may be a live or killed cell and may be a wet or dry bacterium. In the present specification, the term "*bifidobacterium*" means a *bifidobacterium* strain or cell.

In the present invention, examples of the "processed product" of the *bifidobacterium* include, but not limited to, suspensions (or suspension solutions), cultures (containing bacterial cells, culture supernatants, and medium components), culture supernatants (obtained from cultures by removing solid matter), fermented products (*bifidobacterium*-fermented raw milk, skimmed milk, or soymilk; e.g., yogurt), heat-treated products, sterilized product (e.g., a radiation-sterilized product), cell lysates (e.g., an ultrasonic disrupted product), condensates, pastes, dry products (e.g., spray-dried, freeze-dried, vacuum-dried, and drum-dried products), liquid products, and diluted products of the *bifidobacterium*.

In the present invention, the "processed product" of the *bifidobacterium* may be a condensate obtained by condensing the cultures or fermented product, or may be a dried product with a bacterial cell concentration of $10^{10}$ cells/g of dried product obtained by further drying the condensate. This drying of the condensate can be performed by a usual approach, for example, vacuum drying, spray drying, or freeze drying.

The maximum number of bacterial cells contained in the processed product of the *bifidobacterium* of the present invention is not particularly limited, but is usually approximately $4\times10^{10}$ cells/g of condensate or approximately $5\times10^{11}$ cells/g of dried product.

Even the killed cells of the *bifidobacterium* of the present invention can remarkably stimulate IgA production from Peyer's patch cells (see, Examples). Therefore, it may be considered that a component that activates the induction of IgA production is probably contained in the cell wall of the *bifidobacterium* belonging to *Bifidobacterium bifidum*. However, the present invention is not intended to be constrained by such a theory.

A secretory component secreted into the gastrointestinal tract has been thought to suppress by itself infection with infectious *E. coli* or toxinogenic *Clostridium* through binding with these pathogens (J. Med. Biol. 1995, 42: 3-9; and J. Med. Microbiol. 1998, 47: 879-888). Thus, the composition for immunostimulation of the present invention has the effect of reducing the risk of infection with infectious pathogens such as infectious *E. coli* or toxinogenic *Clostridium* by promoting secretory component production.

On the other hand, both IgA production from plasma cells in intestinal mucosa and secretory component production in intestinal epithelial cells have been known to play an important role in secretory IgA production from intestinal mucosal epithelial cells to the outside of the organism (into intestinal lumens). Indeed, in secretory component gene-defective experimental animals, IgA supposed to be secreted into intestinal lumens accumulates in serum (J Exp Med 1999; 190: 915-22). The involvement of environmental stimulation in secretory component expression has also been suggested, and reduction in secretory component expression attributed to malnutrition has been reported (Lab Invest 1998; 78: 1255-66). The composition for immunostimulation of the present invention exhibits an ability to stimulate secretory component production and has a high ability to stimulate IgA production. Therefore, the composition for immunostimulation of the present invention can promote secretory IgA production, for example, by convenient oral administration.

The present invention also relates to a method for enhancing the immunity of a subject by administering (preferably, orally administering) the composition for immunostimulation according to the present invention to the subject. Preferably, this method promotes both secretory component production and IgA production, in the subject that has received the composition for immunostimulation, and as a result, promotes secretory IgA production. In this method, the subject to which the composition for immunostimulation is administered is the same as a subject to which a pharmaceutical composition described later is administered. Preferable examples of the subject include pregnant women, lactating women, infants and toddlers, elderly persons, and patients with reduced immune function. The dose of the composition for immunostimulation of the present application can follow the dose of a pharmaceutical composition described later.

3. Food or Drink Product Comprising the Composition for Immunostimulation

The present invention also relates to a food or drink product supplemented with a composition for immunostimulation which comprises a *bifidobacterium* belonging to *Bifidobacterium bifidum* that has an ability to stimulate secretory component production and a high ability to stimulate IgA production, and/or a processed product of the *bifidobacterium*. In the present specification, the "food or drink product" includes, but not limited to, drink, food, and functional food.

The food or drink product comprising the composition for immunostimulation of the present invention is not particularly limited. Examples of drink comprising the composition for immunostimulation of the present invention can include a drink such as fermented milk (e.g., yogurt), lactic acid bacteria beverage, milk beverage (e.g., coffee milk and fruit milk), tea drink (e.g., green tea, black tea, and oolong tea), fruit/vegetable drink (drink containing the juice of a fruit such as orange, apple, or grape or the juice of a vegetable such as tomato or carrot), alcoholic beverage (e.g., beer, sparkling liquors, and wine), carbonated beverage, and soft drink. Production methods and so on for a variety of drinks can be performed with reference to existing reference books, for example, "Latest edition: Soft Drinks" (2003) (KORIN PUBLISHING Co., Ltd.).

Moreover, food comprising the composition for immunostimulation of the present invention is not particularly limited and may be perishable or processed food. Examples thereof can include various foods such as puddings, jelly, ice creams, cake, candies, pasta, Japanese wheat noodle, fish-paste cake, ham, soy sauce, dressings, mayonnaise, bean curd (Tofu), soups, bread, filleted fishes, processed meats, vegetables, and mushrooms. Examples of food particularly preferable in the present invention include fermented milk and lactic acid bacteria beverage that can deliver the *bifidobacterium* of the present invention alive to the intestine.

Functional food is particularly preferable as a food or drink product comprising the composition for immunostimulation of the present invention. The "functional food" of the present invention means food having predetermined functionality for organisms and includes, for example, so-called general health foods such as food with health claims including food for specified health use (including qualified FOSHU [food for specified health use]) and food with nutrient function claims, food for special dietary uses, dietary supplements, health supplements, supplements (e.g., those having a variety of dosage forms such as tablets, coated tablets, sugarcoated tablets, capsules, and liquids), and beauty food (e.g., diet food). The functional food of the present invention also includes health food to which Health claim based on the food standards of Codex (Joint FAO/WHO Food Standards Programme) is applied.

More specific examples preferable as the functional food of the present invention include food for special dietary uses such as food for sick persons, powdered milk for pregnant/lactating women, baby formula milk, and food for elderly persons. The composition for immunostimulation of the present invention has less potential for side effects and can enhance intestinal immunity that can elicit relatively nonspecific, systemic immune response to a wide range of pathogens or the like. Therefore, the composition for immunostimulation of the present invention is particularly preferably used in formula milk or liquid modified milk for infants with immaturely developed immune function (e.g., the composition for immunostimulation may be added to raw materials for usual infant modified milk) or in food for pregnant or lactating women (e.g., powdered milk for lactating women) and food for elderly persons or sick persons with reduced immune function.

Preferred examples of the functional food of the present invention further include supplements for infants with immaturely developed immune function, and supplements for pregnant/lactating women, elderly persons, or sick persons intended for enhancing or recovering immune function.

Preferred examples of the functional food comprising the composition for immunostimulation of the present invention include food with health claims specified on the basis of Japanese legislation. The system of food with health claims has been instituted specifically toward not only usual foods but also foods having forms such as tablets or capsules, in consideration of both domestic and international trends and consistency with the conventional system of food for specified health use. Under this system, the food with health claims is classified into two types, food for specified health use (licensed on a case-by-case basis) and food with nutrient function claims (standardized). Furthermore, the food with health claims also encompasses a new type such as qualified FOSHU [food for specified health use].

It is preferred that the functional food of the present invention should be useful for immunostimulation. The functional food of the present invention may be shown to be useful for immunostimulation by an indicator (e.g., an increase in the amount of IgA production, increase in the amount of a secretory component production, increase in the amount of secretory IgA, and increase in the number of lymphocytes) showing improvement in immune function, preferably, improvement in intestinal immune (mucosal immune) function. A first object of the functional food of the present invention may be a use other than immunostimulation. The functional food (preferably, food for specified health use or qualified FOSHU [food for specified health use]) of the present invention may have a description or indication stating that it has immunostimulating effect or brings about an indication deeply associated with immunostimulation (e.g., an increase in the amount of a secretory component product). The description or indication stating that it has immunostimulating effect can be an indication approved on the basis of stipulations provided by the system of food with health claims. For example, the functional food of the present invention may have a description stating that it "improves reduced mucosal immune function", "enhances a defending ability against infection", "provides less susceptibility to colds", or "enhances body resistance".

The functional food of the present invention may be in the form of a solid preparation such as a tablet, granule, powder, pill, or capsule, a liquid preparation such as a liquid, suspension, or syrup, or a preparation such as a gel, or may be in the form of a usual food or drink product (e.g., drink, light refreshments, and confectionery).

The amount of the composition for immunostimulation of the present invention added to a food or drink product is not particularly limited and may vary according to circumstances. A specific amount of the composition for immunostimulation added can be determined appropriately by those skilled in the art in consideration of the type of a food or drink product and desired tastes and textures. However, typically, an appropriate amount of the composition for immunostimulation added provides 0.001 to 100% by mass, particularly, 0.1 to 100% by mass in total of the *bifidobacterium* and/or the processed product of the *bifidobacterium* contained in the composition for immunostimulation added.

The composition for immunostimulation of the present invention may be incorporated into a food or drink product by any appropriate method available by those skilled in the art. For example, the composition for immunostimulation of the present invention may be prepared in a liquid, gel, solid, powder, or granule form and then added to a food or drink product. Alternatively, the composition for immunostimulation of the present invention may be mixed or dissolved directly into raw materials for a food or drink product. The composition for immunostimulation of the present invention may be applied to, allowed to cover, infiltrated into, or sprayed onto a food or drink product. The composition for immunostimulation of the present invention may be dispersed uniformly or distributed unevenly in a food or drink product. A capsule or the like containing the composition for immunostimulation of the present invention may be prepared. An edible film, food coating agent, or the like may be wrapped around the composition for immunostimulation of the present invention. Alternatively, the composition for immunostimulation of the present invention may be prepared into a form such as a tablet after the addition of an appropriate excipient and the like. The food or drink product comprising the composition for immunostimulation of the present invention may further be processed. Such a processed food or drink product is also encompassed within the scope of the present invention.

In the production of the food or drink product of the present invention, a variety of additives as routinely used in food or drink products may be employed. Examples of the additives include, but not limited to, color formers (e.g., sodium nitrite), coloring agents (e.g., gardenia pigments and Red 102), flavors (e.g., orange flavors), sweeteners (e.g., stevia and aspartame), preservatives (e.g., sodium acetate and sorbic acid), emulsifiers (e.g., sodium chondroitin sulfate and propylene glycol fatty acid ester), antioxidants (e.g., disodium EDTA and vitamin C), pH adjusters (e.g., citric acid), chemical seasonings (e.g., sodium inosinate), thickeners (e.g., xanthan gum), swelling agents (e.g., calcium carbonate), antifoaming agents (e.g., calcium phosphate), binding agents (e.g., sodium polyphosphate), nutrition-enriching agents (e.g., calcium-enriching agents and vitamin A), and excipients (e.g., water-soluble dextrin). Functional raw materials such as *Panax ginseng* extracts, *Acanthopanax senticosus* Harms extracts, eucalyptus extracts, or du zhong tea extracts may further be added.

4. Pharmaceutical Composition Comprising the Composition for Immunostimulation

The present invention also relates to a pharmaceutical composition comprising, as an active ingredient, a composition for immunostimulation which comprises a *bifidobacterium* belonging to *Bifidobacterium bifidum* that has an ability to stimulate secretory component production and a high ability to stimulate IgA production, and/or a processed product of the *bifidobacterium*.

The pharmaceutical composition of the present invention may comprise pharmaceutically acceptable carriers or additives. Examples of such carriers and additives include water, pharmaceutically acceptable organic solvents, collagen, polyvinyl alcohol, polyvinyl pyrrolidone, carboxyvinyl polymers, sodium alginate, water-soluble dextran, water-soluble dextrin, carboxymethyl starch sodium, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, lactose, surfactants acceptable as pharmaceutical additives, and artificial cellular constructs such as liposome. The additives used are selected appropriately or in combination according to the dosage form of the preparation. The pharmaceutical composition of the present invention may further comprise other pharmacological ingredients.

The pharmaceutical composition of the present invention can be administered orally or parenterally. It is particularly preferred that the pharmaceutical composition of the present invention is administered orally. The pharmaceutical composition of the present invention for oral administration may be in a dosage form such as a solid preparation such as a tablet, granule, powder, pill, or capsule, a gel preparation, or a liquid preparation such as a solution, suspension, or syrup. The pharmaceutical composition of the present invention, when used as a liquid preparation, may be provided as a dried product intended for being reconstructed for use of the pharmaceutical composition of the present invention.

Of the dosage forms, an oral solid preparation may comprise additives generally pharmacologically used such as binders, excipients, lubricants, disintegrants, and wetting agents. Alternatively, an oral liquid preparation may comprise additives generally pharmacologically used such as stabilizers, buffers, corrigents, preservatives, flavors, and coloring agents.

It is preferred that the pharmaceutical composition of the present invention should exhibit immunostimulating effect. The pharmaceutical composition of the present invention may be obtained by additionally imparting immunostimulating effect to a pharmaceutical composition for a different therapeutic use comprising another pharmacological substance. Alternatively, the pharmaceutical composition of the present invention is, preferably, an immunostimulant agent.

The pharmaceutical composition of the present invention can enhance the immune system, particularly, the mucosal immune system, by significantly increasing the amount of IgA produced in the mucosal immune system and increasing the amount of a secretory component produced. The pharmaceutical composition of the present invention can be used, for example, for the purpose of enhancing a defending ability against infection with pathogens.

The dose of the pharmaceutical composition of the present invention may vary depending on the age and body weight of a subject to which the pharmaceutical composition of the present invention is administered, an administration route, the number of doses, and can be changed extensively at the discretion of those skilled in the art. For example, for oral administration, an appropriate dose of the *bifidobacterium* and/or the processed product of the *bifidobacterium* contained in the composition for immunostimulation added in the pharmaceutical composition is 1 to 1000 mg/kg/day. The pharmaceutical composition of the present invention may be administered at a single dose or may be administered repeatedly at 6- to 8-hour intervals.

The subject to which the pharmaceutical composition of the present invention is administered is a mammal including humans, livestock, pet animals, experimental (test) animals. Particularly, an infant mammal with immaturely developed immune function, a mammal with immune function reduced due to aging or disease, or a mammal susceptible to reducing immune function due to constitutional or environmental factors is preferable as a subject to which the pharmaceutical composition of the present invention is administered. The pharmaceutical composition of the present invention has less potential for side effects and therefore, can be used very usefully for continuous use.

All publications, patents, and patent applications cited herein are incorporated herein by reference in their entirety.

EXAMPLES

Hereinafter, the present invention will be described with reference to Examples. However, the technical scope of the present invention is not intended to be limited to them.

Example 1

Assay of the Abilities of Bifidobacteria to Stimulate IgA Production

1. Preparation of Bifidobacteria

*Bifidobacterium longum* OLB 6001 strain (accession No. FERM P-13610), *Bifidobacterium bifidum* OLB 6377 strain (accession No. NITE BP-30), *Bifidobacterium bifidum* OLB 6378 strain (accession No. NITE BP-31), a *Bifidobacterium breve* strain (accession No. FERM BP-2824), and *Bifidobacterium bifidum* MEP170212 strain (former name: *Bifidobacterium bifidum* #1 (Meiji) strain, which is possessed by Meiji Dairies Corp. (Japan)) were separately cultured overnight at 37° C. in an anaerobic EG medium prepared by using lactose instead of glucose. The anaerobic EG medium was prepared according to the following composition:

| Composition of anaerobic EG medium 40.0 g (per litter) | |
|---|---|
| Meat extracts | 2.6 g |
| Proteose peptone | 10.0 g |
| Yeast extracts | 5.0 g |
| Sodium monohydrogen phosphate | 4.0 g |
| Lactose | 1.5 g |
| Soluble starch | 0.5 g |
| L-cystine | 0.2 g |
| L-cysteine hydrochloride | 0.5 g |
| Antifoaming agent (silicone) | 0.2 g |
| Polysorbate 80 | 0.5 g |
| Agar | 15.0 g |
| pH | 7.7 |

The bacterial cells in each of the resulting cultures were washed twice with cold PBS(−) and then suspended in a small amount of PBS(−) and then in an equal amount of 8% formalin-PBS to fix the bacterial cells. Formalin was removed from the fixed bacterial cells by washing with cold PBS(−) on the day of the assay experiment of the ability to stimulate IgA production, and then the resultant bacterial solution was suspended in PBS to adjust its concentration to a level corresponding to a turbidity of 1.6 at 660 nm. The bacterial solutions thus obtained were designated as formalin-treated *bifidobacterium* solutions.

2. Assay of the Abilities of Bifidobacteria to Stimulate IgA Production from Peyer's Patch Cells An 8-week-old BALB/c mouse (female) was killed by exposure to a carbon dioxide stream for 50 seconds. Peyer's patch was collected from the small intestine aseptically excised from the mouse. This Peyer's patch was taken into an RPMI-1640 medium (Gibco) containing a small amount of 2% bovine fetal serum. Peyer's patch cells were prepared by a partial modification of the method of Suzuki et al (Slide method; Bifidobacteria Microflora, 9: 87-98, 1990). Specifically, the collected Peyer's patch was taken onto a petri dish containing an RPMI-1640 medium (Gibco) containing a small amount of 2% bovine fetal serum, minced with the edge of a dissecting knife, and gradually broken up during pressing with the handle of a plastic syringe (Terumo). The resulting cell suspension was passed through a 150-gauge sterile stainless steel sieve and further washed twice with an RPMI-1640 medium containing 2% bovine fetal serum. The cells were resuspended in an RPMI-1640 medium containing an appropriate amount of 2% bovine fetal serum to obtain lymphoid cell population (Peyer's patch cells) including T and B cells.

The obtained lymphoid cell population was washed by changing the RPMI-1640 medium twice. While trypan blue was used to confirm that 98% or more cells were live cells, these cells were seeded at a density of $5 \times 10^5$ cells/well in a 96-well microplate (Falcon 3072). This 96-well microplate used was coated in advance with an anti-CD3 antibody (CEDARLANE, No. CL7202AP, concentration used: 2.5 μg/ml) by incubating, at 37° C. for 2 hours, the microplate containing in advance 100 μl/well of the anti-CD3 antibody, and then washing it once with 200 μl of PBS and subsequently once with 200 μl of FCS(−) RPMI medium.

Further, the formalin-treated *bifidobacterium* solutions (with a turbidity of 1.0) derived from those five strains as prepared according to the above section "1. Preparation of bifidobacteria" were respectively added at a concentration of 5 μl/well to three wells of the 96-well microplate seeded with the lymphoid cell population, and cultured at 37° C. for 5 days in a carbon dioxide incubator. The cultured bacterial solutions were centrifuged at 1400 rpm for 10 minutes to remove the lymphoid cell population, and the resulting culture supernatants were stored at −80° C. until assay, as samples to be subjected to IgA amount determination. Subsequently, IgA amounts in the culture supernatant samples were determined with a Mouse IgA ELISA Quantitation Kit (Bethyl laboratories) according to the method described in its instructions.

On the other hand, as a control experiment, the lymphoid cell population was cultured for 5 days in the presence of an anti-CD3 antibody in the same way as above except that no formalin-treated *bifidobacterium* solution was added. The IgA amount in the culture supernatant was determined in the same way as above.

The determined IgA concentrations in the culture supernatants are shown in Table 1.

TABLE 1

| Sample | Strain | Anti-CD3 antibody | IgA amount (μg/ml) |
|---|---|---|---|
| Anti-CD3 (−) | Absent | − | 0.42 |
| Anti-CD3 (+) | Absent | + | 3.84 |
| 1 | *B. longum* OLB 6001 | + | 4.21 |
| 2 | *B. breve* strain (accession No. FERM BP-2824) | + | 3.67 |
| 3 | *B. bifidum* OLB 6377 | + | 10.5 |
| 4 | *B. bifidum* OLB 6378 | + | 16.8 |
| 5 | *B. bifidum* MEP170212 | + | 5.73 |

Figure 1:
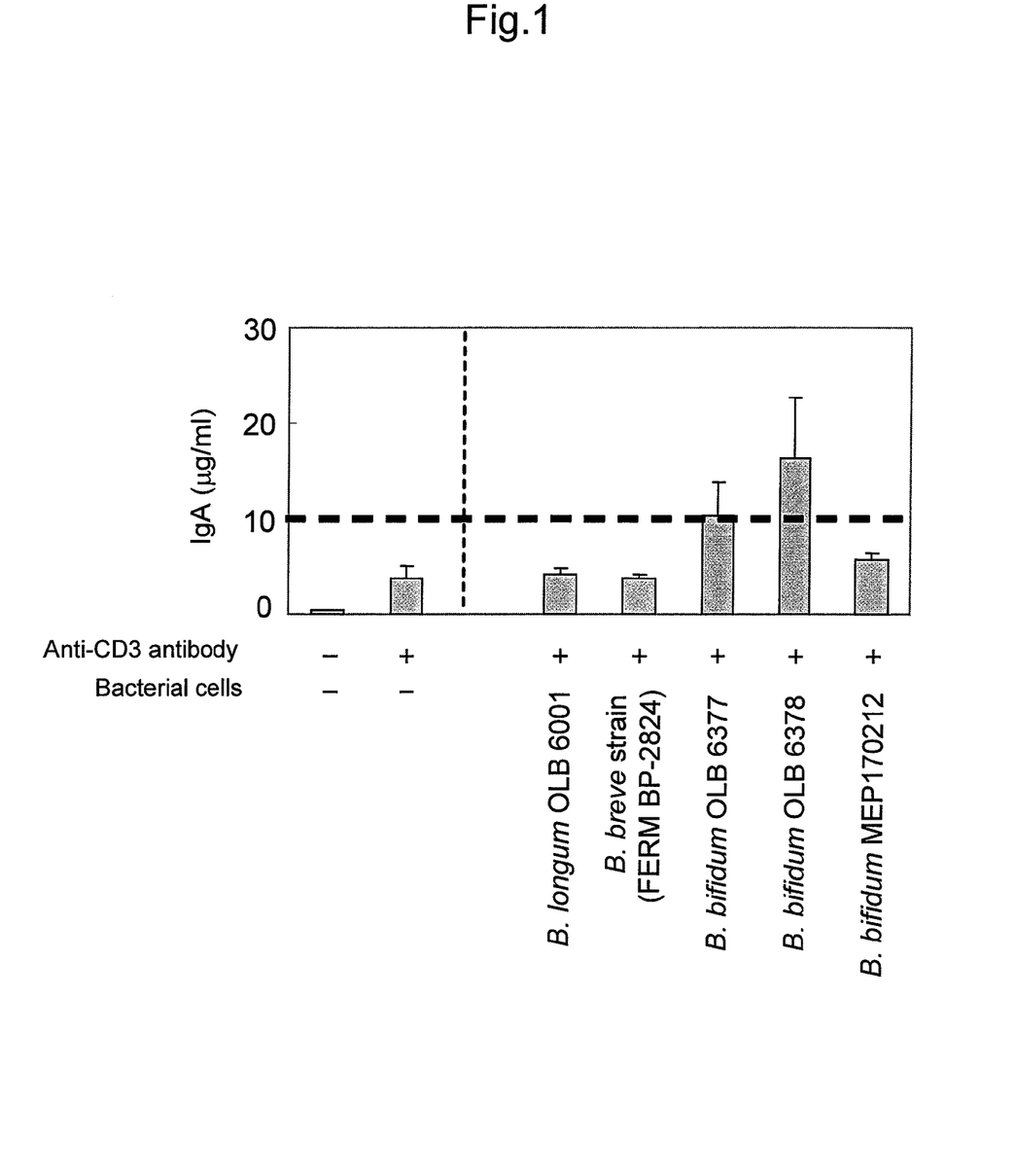
FIG. 1 shows the abilities of various bifidobacteria to stimulate IgA production, which were observed when lymphoid cell population derived from mouse Peyer's patch were cultured with the bifidobacteria in the presence of an anti-CD3 antibody. The value is indicated with an average±standard deviation (n=3).

The results are shown in a graph form in FIG. 1 on the basis of Table 1.

As shown in the left section of the graph of FIG. 1, the lymphoid cell population (Peyer's patch cells) cultured for 5 days in the presence of an anti-CD3 antibody secreted IgA into the culture supernatant. This demonstrates that IgA-producing cells (plasma cells) are differentiated in the Peyer's patch cells cultured in the presence of an anti-CD3 antibody.

As shown in Table 1 and the right section of the graph of FIG. 1, the use of the present assay system showed that the *Bifidobacterium bifidum* OLB 6377 and *Bifidobacterium bifidum* OLB 6378 strains have an ability to stimulate IgA production 2 to 5 times larger than those of the *Bifidobacterium longum* OLB 6001 strain (accession No. FERM P-13610) and the *Bifidobacterium breve* strain (accession No. FERM BP-2824) that were previously reported to have an ability to stimulate IgA production.

Example 2

Assay of the Abilities of Bifidobacteria to Stimulate Secretory Component Production-I 1. Preparation of Cell Lysates of Bifidobacteria

*Bifidobacterium bifidum* OLB 6377 strain, *Bifidobacterium bifidum* OLB 6378 strain, *Bifidobacterium bifidum* MEP170212 strain (former name: *Bifidobacterium bifidum* #1 (Meiji) strain, which is possessed by Meiji Dairies Corp. (Japan)), and *Bifidobacterium bifidum* MEP170222 strain (former name: *Bifidobacterium bifidum* #2 (Meiji) strain, which is possessed by Meiji Dairies Corp. (Japan)) were separately cultured overnight in an anaerobic EG medium prepared by using lactose instead of glucose, in the same way as in Example 1. Subsequently, the bacterial cells in each of the resulting cultures were washed twice with cold PBS(−) and then suspended at a concentration of 10 mg/ml in PBS(−). Each suspension was heat-treated at 75° C. for 60 minutes and then subjected to an ultrasonic disintegrator (BRANSON SONIFIER 250, Duty cycle: 60%, Output control: 2 micro tip limit) to obtain a bacterial cell lysate.

2. Assay of the Abilities of Cell Lysates of the Bifidobacterium to Stimulate Secretory Component Production from HT-29 Cells HT-29 cells derived from human intestinal epithelial cells were seeded at a density of approximately 3 to $6 \times 10^5$ cells/well in a 12-well plate. To the well, 1.0 ml of McCoy's 5A medium (Invitrogen) containing 10% bovine fetal serum was added. The next day, the cell lysates of those four *bifidobacterium* strains (*Bifidobacterium bifidum* OLB 6377 strain, *Bifidobacterium bifidum* OLB 6378 strain, *Bifidobacterium bifidum* MEP170212 strain, and *Bifidobacterium bifidum* MEP170222 strain) prepared according to the section "1. Preparation of cell lysates of bifidobacteria" were respectively added at a concentration of 50 to 500 μg/ml/well to the media in three wells of the 12-well plate prepared as described above and cultured at 37° C. for 48 hours. As a control experiment, PBS(−) [Dulbecco's Phosphate Buffered Saline without Ca and Mg ions] was used instead of the bacterial cell lysates. Culture supernatants were collected from the resulting cultures. Secretory component concentrations in the culture supernatants were determined by an ELISA method. For this ELISA method, the wells of an ELISA plate were first coated overnight at 4° C. with a polyclonal antibody against the human secretory component (DAKO; used after 1000-fold dilution with PBS(−)) and then washed with PBS(−) supplemented with 0.01% Tween 20. Subsequently, 1% bovine serum albumin (BSA)-PBS(−) was added to the plate, followed by incubation at room temperature for 1 hour to block the plate. Next, 50 μl each of the thus-obtained culture supernatants was added as a sample to each well of this plate and incubated at room temperature for 1 hour. Each well was washed with PBS(−) supplemented with 0.01% Tween 20. Then, horseradish peroxidase-labeled anti-human secretory component antibodies (DAKO; used after 1000-fold dilution with 1% BSA-PBS(−)) was added thereto, followed by incubation of the plate at room temperature for 30 minutes. Subsequently, each well was washed with PBS(−) supplemented with 0.01% Tween 20. Then, 100 μl of aqueous solution of ortho-phenylenediamine/hydrogen peroxide was added to each well, followed by reaction for 30 minutes. After reaction, the reaction was terminated by the addition of 20 μl of $2NH_2SO_4$. Then, absorbance was measured at a measurement wavelength of 490 nm. The measurement results were expressed by relative values to that of the amount of a secretory component produced in the control defined as 1. A significant difference test between the groups was conducted by Student's t-test to determine the presence or absence of the significant difference with a significance level of 5% or less.

Figure 2:
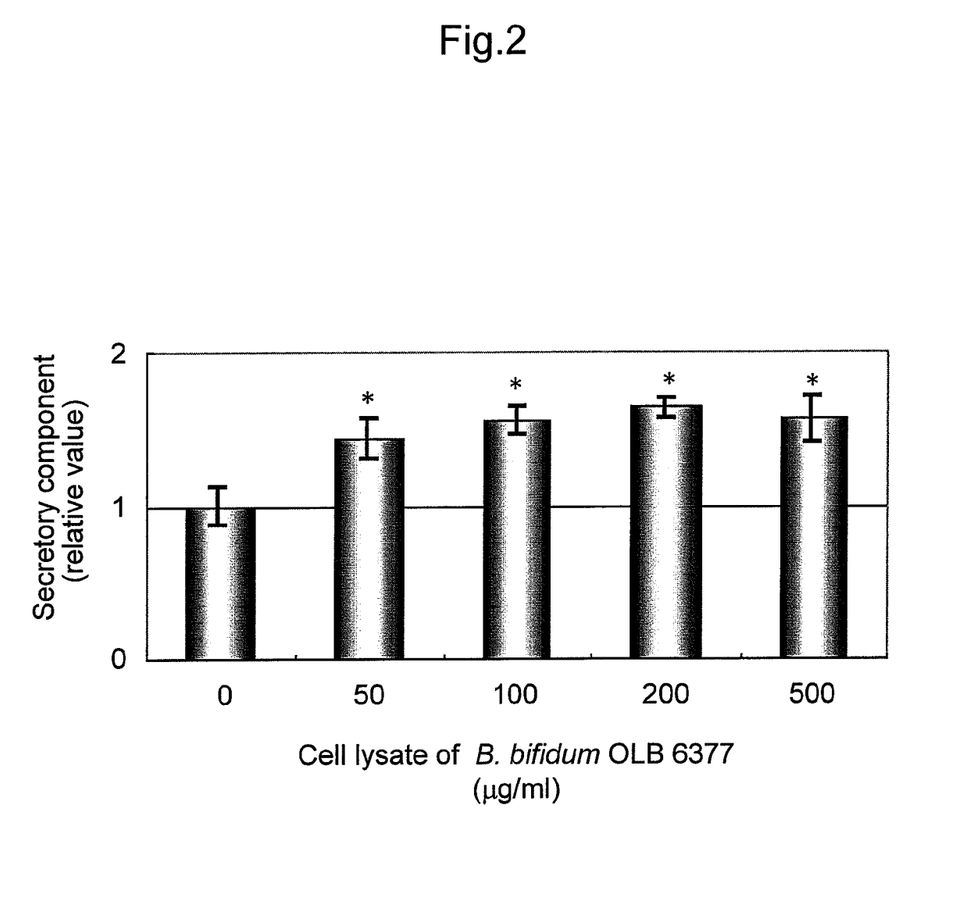
FIG. 2 shows the effect of cell lysate of *Bifidobacterium bifidum* OLB 6377 strain on secretory component production from HT-29. The sample was added at a concentration of 50 to 500 μg/ml to a medium and cultured for 48 hours. *p<0.05 vs. control group, Student's t-test (n=3). The value is determined as a relative value to a control defined as 1, and indicated with an average±standard deviation.

Table 2 and FIG. 2 show the secretory component measurement results for the cell lysate of *Bifidobacterium bifidum* OLB 6377 strain added in varying amounts (50 μg/ml, 100 μg/ml, 200 μg/ml, and 500 μg/ml) to the medium in the above assay.

TABLE 2

| Amount of cell lysate of *B. bifidum* OLB 6377 added (μg/ml) | Relative value of secretory component amount |
|---|---|
| 0 | 1.00 |
| 50 | 1.44 |
| 100 | 1.55 |
| 200 | 1.63 |
| 500 | 1.57 |

As a result, the addition of the bacterial cell lysate even at a concentration of 50 μg/ml exhibited approximately 1.4-fold increase in the amount of a secretory component produced, compared with that of the control. Even though the amount of the cell lysates added was increased, only a similar level of increase in the amount of a secretory component produced was shown (FIG. 2).

These results also showed that the bifidobacteria according to the present invention even in the case of a cell lysate of the bacteria inactivated by heat treatment at 75° C. for 60 minutes has the effect of promoting secretory component production.

Figure 3:
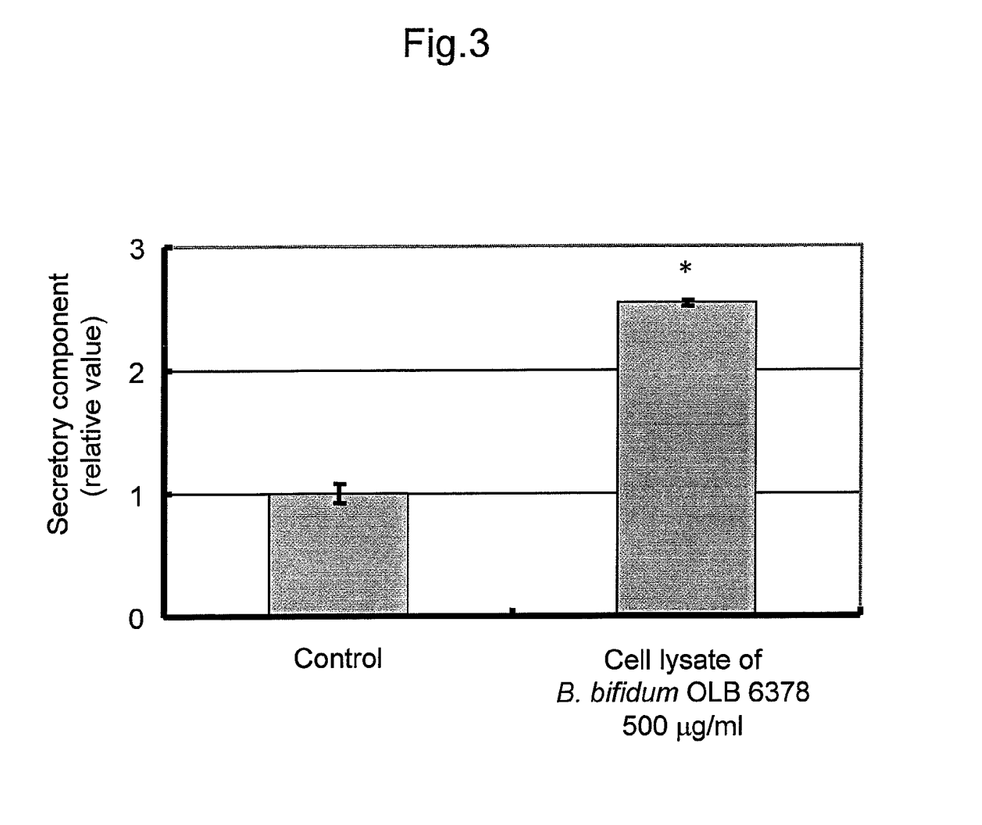
FIG. 3 shows the effect of cell lysate of *Bifidobacterium bifidum* OLB 6378 strain on secretory component production from HT-29 cells. The sample was added at a concentration of 500 μg/ml to a medium and cultured for 48 hours. *p<0.05 vs. control group, Student's t-test (n=3). The value is determined as a relative value to a control defined as 1, and indicated with an average standard deviation.

Moreover, Table 3 and FIG. 3 show secretory component measurement results for the cell lysate of *Bifidobacterium bifidum* OLB 6378 strain added at a concentration of 500 μg/ml to the medium in the above assay.

TABLE 3

| Sample | Relative value of secretory component amount |
|---|---|
| Control | 1.00 |
| 500 μg/ml cell lysate of *B. bifidum* OLB 6378 | 2.54 |

As shown in Table 3 and FIG. 3, the addition of 500 μg/ml of the cell lysate of *Bifidobacterium bifidum* OLB 6378 strain exhibited approximately 2.5-fold increase in the amount of a secretory component produced, compared with that of the control.

Figure 4:
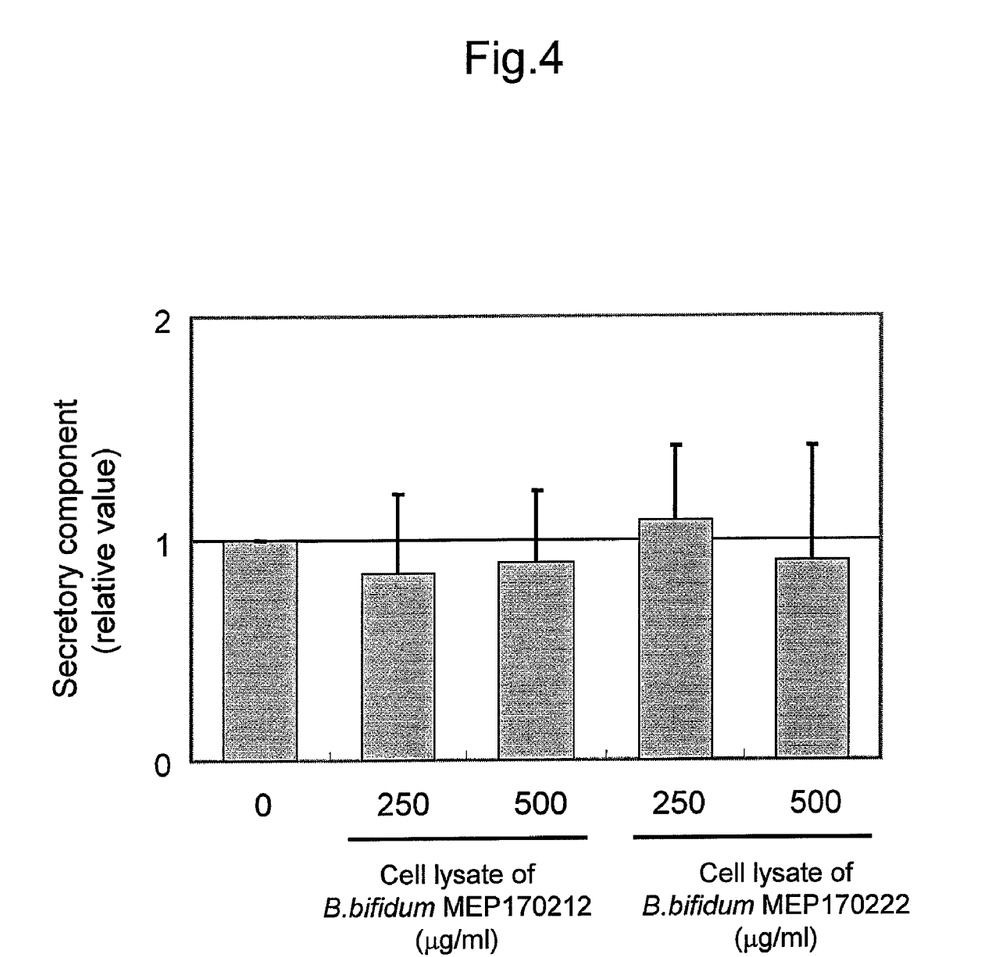
FIG. 4 shows the effect of cell lysates of *Bifidobacterium bifidum* MEP170212 and *Bifidobacterium bifidum* MEP170222 on secretory component production from HT-29 cells. The sample was added at a concentration of 250 μg/ml or 500 μg/ml to a medium and cultured for 48 hours. No significant difference between the groups at 5% level by Student's t-test (n=3). The value is determined as a relative value to a control defined as 1, and indicated with an average±standard deviation.

Furthermore, Table 4 and FIG. 4 show secretory component measurement results for the cell lysates of *Bifidobacterium bifidum* MEP170212 strain and *Bifidobacterium bifidum* MEP170222 strain added at a concentration of 250 μg/ml and 500 μg/ml to the medium in the above assay.

TABLE 4

| Sample | Relative value of secretory component amount |
|---|---|
| Control | 1.00 |
| 250 μg/ml cell lysate of *B. bifidum* MEP170212 | 0.84 |
| 500 μg/ml cell lysate of *B. bifidum* MEP170212 | 0.89 |
| 250 μg/ml cell lysate of *B. bifidum* MEP170222 | 1.09 |
| 500 μg/ml cell lysate of *B. bifidum* MEP170222 | 0.90 |

As shown in FIG. 4, the addition of *Bifidobacterium bifidum* MEP170212 and *Bifidobacterium bifidum* MEP170222 even at the relatively high concentration of 250 μg/ml exhibited no increase in the amount of secretory component production. This demonstrates that not all of bifidobacteria belonging to *Bifidobacterium bifidum* have an ability to enhance secretory component production.

Example 3

Assay of Secretory Component Gene Expression Level in Organ-Cultured Tissues of Small Intestine and Large Intestine, after Treated with Cell Lysate of the *Bifidobacterium*

The ileum and proximal large intestine were excised from a BALB/c mouse within 24 hours after birth and used in study after organ culture. Specifically, the ileum and proximal large intestine were cut into round slices to prepare tissue sections of approximately 2 to 4 mm in width. The tissue sections were cut in a longitudinal direction into a sheet on a glass filter paper, and the muscularis mucosae sides thereof were adhered tightly to the glass filter paper. The prepared tissue sheets were placed into a 48-well plate. To the well, 0.5 ml of RPMI medium (Nissui Pharmaceutical) containing 100 U/ml penicillin (Banyu Pharmaceutical), 0.1 mg/ml streptomycin (Meiji Seika), 0.05 mg/ml gentamycin (LIFE TECHNOLOGIES), and 10% bovine fetal serum was added.

Subsequently, a cell lysate of *B. bifidum* OLB 6378 strain prepared according to the section "1. Preparation of cell lysates of bifidobacteria" of Example 2 was added at a concentration of 500 μg/ml/well to the media in three wells of the 48-well plate prepared as described above and cultured at 37° C. for 18 hours (n=3). As a control experiment, PBS(−) was used (n=3) instead of the bacterial cell lysate.

After the completion of culture, total RNA was extracted from the cultured tissues by use of an RNA purification kit (QIAGEN, RNeasy mini kit) and used as a template to prepare cDNA with an oligo dT primer (INVITROGEN). The cDNA was further used as a template to perform real-time PCR using PCR primers (5'-AGGCAATGACAA-CATGGGG-3' (SEQ ID NO: 1) and 5'-ATGTCAGCTTC-CTCCTTGG-3' (SEQ ID NO: 2)) specific to pIgR gene (secretory component gene) in a LightCycler (Roche) to determine the expression level of pIgR gene in the prepared cDNA. The pIgR gene expression level determined for each sample was corrected based on the expression level of GAPDH gene, one of house keeping genes, which was detected in the same way using PCR primers 5'-TGAACGG-GAAGCTCACTGG-3' (SEQ ID NO: 3) and 5'-TCCAC-CACCCTGTTGCTGTA-3' (SEQ ID NO: 4). The correction is performed according to the following calculation formula:

Relative pIgR gene expression level=pIgR gene expression level/GAPDH gene expression level.

Figure 5:
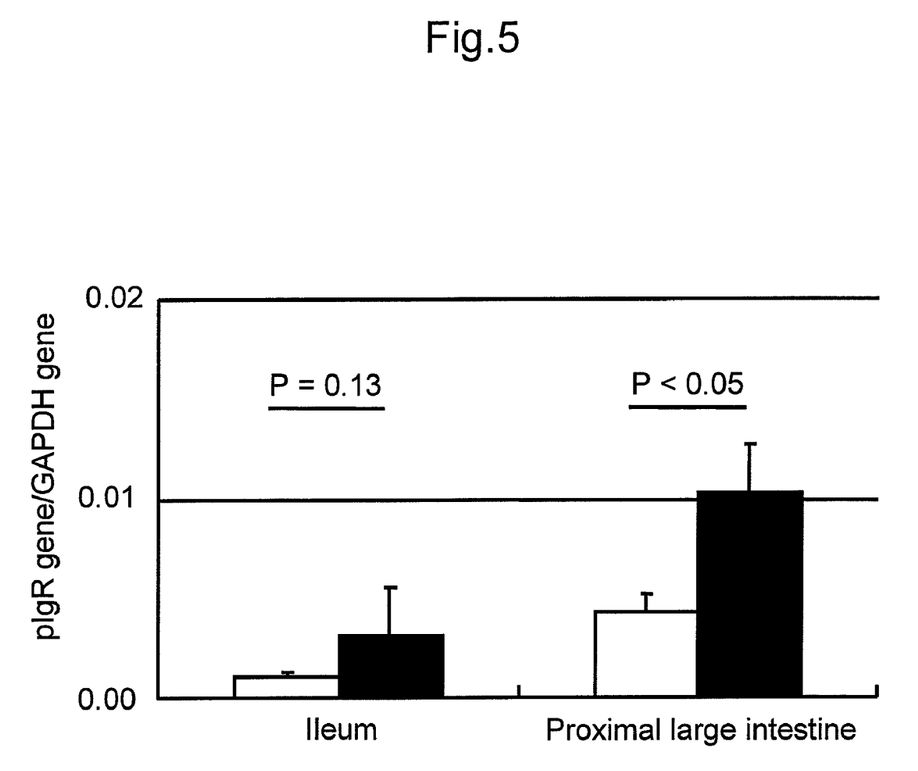
FIG. 5 shows the effect of cell lysate of a *Bifidobacterium bifidum* OLB 6378 strain on secretory component gene expression levels in the small intestine and large intestine. The bar denotes a relative value indicated with an average±SD (standard deviation).

Table 5 and FIG. 5 show the average relative pIgR gene expression level of multiple experimental samples on the basis of the relative pIgR gene expression levels thus calculated.

TABLE 5

|  | Control | Cell lysate of B. bifidum OLB 6378 (500 µg/ml) |
|---|---|---|
| Ileum | 0.0011 | 0.0031 |
| Proximal large intestine | 0.0042 | 0.0102 |

In FIG. 5, the white bar denotes the relative pIgR gene expression level in the control experiment, and the black bar denotes the relative pIgR gene expression level for addition of the cell lysates of *Bifidobacterium bifidum* OLB 6378 strain. Also, one standard deviation is indicated for each bar.

As shown in Table 5 and FIG. 5, the addition at a concentration of 500 µg/ml of the bacterial cell lysate of *Bifidobacterium bifidum* OLB 6378 strain prepared according to Example 2 exhibited 2.9-fold increase in the ileum (lower part of the small intestine) and 2.4-fold increase in the proximal large intestine (initial portion of the large intestine) in the expression level of pIgR gene (secretory component gene), compared with that of the control. A significant difference was confirmed by Mann-Whitney U-test in the increase observed in the large intestine (P<0.05). This demonstrates that bacterial cell lysates of *Bifidobacterium bifidum* enhance secretory component gene expression in the small intestine and large intestine.

Example 4

DNA Microarray Assay of Secretory Component Gene Expression Level and IRF-1 Gene Expression Level in Organ-Cultured Tissues of Small Intestine and Large Intestine Treated with Cell Lysate of *Bifidobacterium*

The ileum and proximal large intestine were excised from an embryonic day 18 BALB/c mouse and used in study after organ culture. The ileum and proximal large intestine were cut into round slices to prepare tissue sections of approximately 2 to 4 mm in width in the same way as in Example 3. The tissue sections were cut in a longitudinal direction into a sheet on a glass filter paper, and the muscularis mucosae sides thereof were adhered tightly to the glass filter paper. The prepared tissue sheets were placed into a 48-well plate. To the well, 0.5 ml of DMEM medium (Gibco) containing 100 U/ml penicillin (Banyu Pharmaceutical), 0.1 mg/ml streptomycin (Meiji Seika), 0.05 mg/ml gentamycin (LIFE TECHNOLOGIES), and 10% bovine fetal serum was added.

Subsequently, a cell lysate of *B. bifidum* OLB 6378 strain prepared according to the section "1. Preparation of cell lysates of bifidobacteria" of Example 2 was added at a concentration of 500 µg/ml/well to the media in three wells of the 48-well plate prepared as described above and cultured at 37° C. for 18 hours. As a control experiment, PBS(−) was used (n=3) instead of the bacterial cell lysate.

After the completion of culture, total RNA was extracted from the cultured tissues by use of an RNA purification kit (QIAGEN, RNeasy mini kit). The total RNAs derived from those three wells were combined together and used in the assay described below. The total RNA was used as a template to synthesize fragmented cRNA by use of a GeneChip One-Cycle Target Labeling and Control Reagents kit (Affymetrix). In Particular, cDNA was synthesized by use of a GeneChip Expression 3'-Amplification Reagent One-Cycle cDNA Synthesis Kit (Affymetrix) and GeneChip Eukaryotic Poly-A RNA Control Kit (Affymetrix) included in the kit. Next, the resulting cDNA was purified by use of a GeneChip Cleanup Module (Affymetrix), and in vitro transcription reaction was carried out with a GeneChip Expression 3'-Amplification Reagent IVT labeling Kit (Affymetrix). The resultant cRNA was purified with a GeneChip Cleanup Module (Affymetrix) and then subjected to fragmentation treatment using a Fragmentation buffer (Affymetrix) to obtain fragmented cRNA. The fragmented cRNA was used to conduct analysis using a DNA Array system (Affymetrix). A mouse genome MG U74Av2 set (Affymetrix) containing approximately 36,000 mouse genes was used herein as probes for DNA array. The variation between experiments was corrected using the ratio of the gene expression to the internal control. The effect of treatment with the *B. bifidum* OLB 6378 strain on each gene expression level is indicated as a ratio to each gene expression level in a control experiment (PBS(−) treatment).

As a result, an increase in the expression level of the secretory component gene (pIgR gene) in the organ-cultured tissues of the small intestine and large intestine as well as an increase in the expression level of the IRF-1 gene, an intracellular signaling factor, was confirmed (Table 6).

TABLE 6

|  | Control | Cell lysate of B. bifidum OLB 6378 (500 µg/ml) |
|---|---|---|
| (pIgR gene expression level) | | |
| Ileum | 1.0 | 2.0 |
| Proximal large intestine | 1.0 | 6.1 |
| (IRF-1 gene expression level) | | |
| Ileum | 1.0 | 1.5 |
| Proximal large intestine | 1.0 | 4.0 |

As shown in Table 6, the addition at a concentration of 500 µg/ml of the cell lysate of the *Bifidobacterium bifidum* OLB 6378 strain prepared according to Example 2 exhibited 2.0-fold increase in the ileum (lower part of the small intestine) and 6.1-fold increase in the proximal large intestine (initial portion of the large intestine) in the expression level of the secretory component gene (pIgR gene), compared with that of the control, which were almost equal to the results of Example 3. Furthermore, the addition of the cell lysate of the *Bifidobacterium bifidum* OLB 6378 strain exhibited 1.5-fold increase in the ileum and 4.0-fold increase in the proximal large intestine (initial portion of the large intestine) in the expression level of the IRF-1 gene, compared with that of the control.

IRF-1 has been shown to be one of transcriptional factors for the secretory component gene (Blanch et al. J Immunol 1999, 162: 1232-1235). Thus, the induction of secretory component gene expression by treatment with the *B. bifidum* OLB 6378 strain was demonstrated to be enhanced via the intracellular signaling pathway.

Example 5

Assay of the Abilities of Bifidobacteria to Stimulate Secretory Component Production-II The abilities to stimulate secretory component production were assayed for bifidobacteria *Bifidobacterium bifidum* OLB 6378 and *Bifidobacterium bifidum* JCM $1255^T$ strains basically according to the method of Example 2 and then compared. The *Bifidobacterium bifidum* JCM $1255^T$ strain was obtained as a strain for comparison from Japan Collection of Microorganisms (JCM), Riken Bioresource Center (2-1 Hirosawa, Wako, Saitama, Japan).

The *Bifidobacterium bifidum* OLB 6378 and *Bifidobacterium bifidum* JCM $1255^T$ strains were separately cultured overnight, then washed twice with cold PBS(−), and suspended in PBS(−), according to the procedure of Example 2. Each suspension was added in an amount of 500 μg/ml in terms of bacterial cell concentration to a medium (McCoy's 5A medium (Invitrogen) containing 10% bovine fetal serum) seeded with HT-29 cells as prepared according to the procedure of Example 2, and cultured at 37° C. for 72 hours (n=2). Culture supernatants were collected from the resulting cultures on 48 and 72 hours. Secretory component concentrations in the respective culture supernatants were determined by an ELISA method according to the procedure of Example 2.

As a control experiment, PBS(−) instead of the bacterial cell suspensions in PBS(−) was added to the medium described above (in Table 7 below, "PBS(−)"). As an additional control experiment, the medium described above was cultured without adding bacterial cell suspensions in PBS(−) and other alternative substances (in Table 7 below, "Medium alone").

Figure 6:
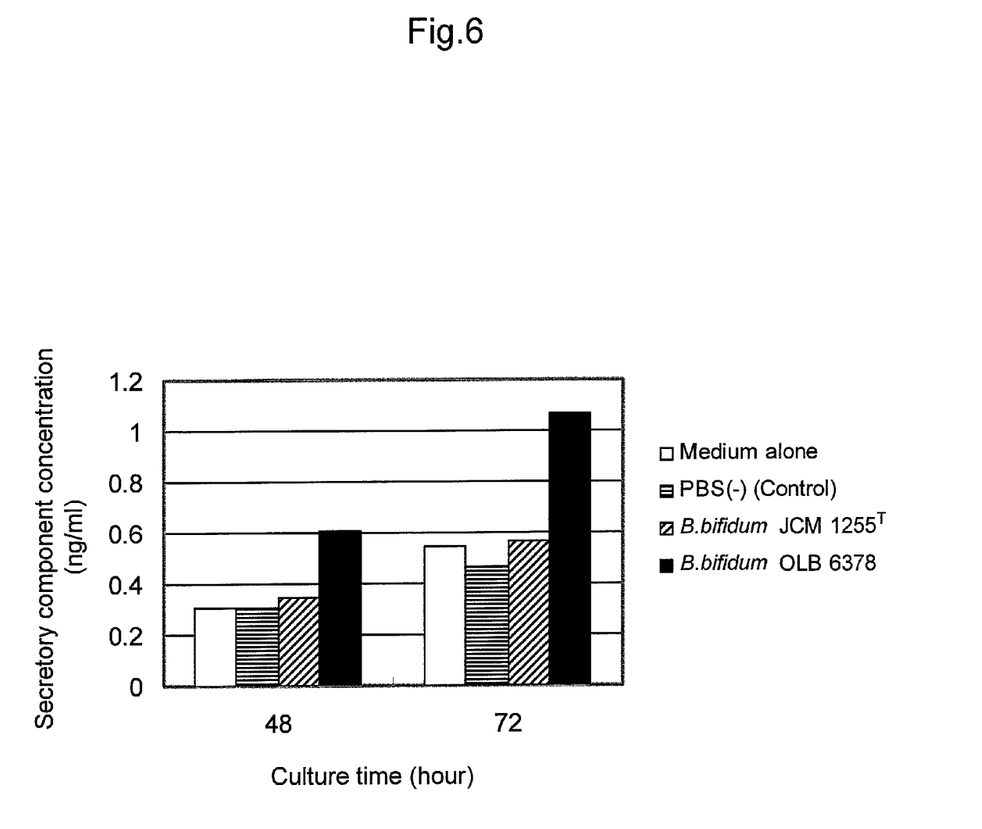
FIG. 6 shows the effect of *Bifidobacterium bifidum* OLB 6378 strain on secretory component production from HT-29 cells in terms of a secretory component concentration (ng/ml).

The results are shown in Table 7 and FIG. 6. The secretory component concentration shown in Table 7 is the average value of n=2.

TABLE 7

| | Secretory component concentration (ng/ml) | |
|---|---|---|
| | on 48 hours | on 72 hours |
| Medium alone | 0.31 | 0.55 |
| PBS(−) | 0.31 | 0.47 |
| *B. bifidum* JCM $1255^T$ | 0.35 | 0.57 |
| *B. bifidum* OLB 6378 | 0.61 | 1.07 |

As shown in Table 7 and FIG. 6, the HT-29 cells produced a secretory component even without stimulation. Furthermore, the *Bifidobacterium bifidum* OLB 6378 strain could stimulate the production of a remarkably large amount of a secretory component, compared with that of the *Bifidobacterium bifidum* JCM $1255^T$ strain.

INDUSTRIAL APPLICABILITY

A composition for immunostimulation of the present invention can particularly enhance the function of the mucosal immune system by promoting secretory component production and highly promoting IgA production. Thus, the composition for immunostimulation of the present invention is useful in imparting such effect of enhancing immune function to a food or drink product or a pharmaceutical composition. A food or drink product or a pharmaceutical composition comprising the composition for immunostimulation of the present invention is suitable for use in patients with reduced immune function, for example, infants, elderly persons, and sick persons. Moreover, the composition for immunostimulation of the present invention can be produced by use of killed cells of a *bifidobacterium* of the present invention. Therefore, the composition for immunostimulation of the present invention can be used even in products for which biological specifications are established, such as infant formula milk, and can be utilized in various products, regardless of product forms.

Free Text of Sequent Listing
SEQ ID NOS: 1 to 4: primer sequences

The invention claimed is:

1. A composition for immunostimulation comprising a *Bifidobacterium* belonging to *Bifidobacterium bifidum* and/or a processed product of the *Bifidobacterium*, wherein said *Bifidobacterium* has an ability to stimulate secretory component production so as to increase the amount of secretory component production in an intestinal epithelial cell by at least 1.2 times, wherein the secretory component is a component of secretory IgA, and wherein said *Bifidobacterium* is *Bifidobacterium bifidum* OLB 6377 strain, Accession No. NITE BP-30 or *Bifidobacterium bifidum* OLB 6378 strain, Accession No. NITE BP-31.

2. The composition for immunostimulation according to claim 1, wherein said processed product of the *bifidobacterium* is at least one selected from the group consisting of suspensions, cultures, culture supernatants, fermented products, heat-treated products, cell lysates, concentrates, pastes, dried products, and diluted products of the *bifidobacterium*.

3. A food or drink product comprising the composition for immunostimulation according to claim 1.

4. The food or drink product according to claim 3, wherein the food or drink is selected from the group consisting of baby foods, infant foods, foods for lactating women, foods for elderly persons, foods for sick persons, foods with health claims, supplements, fermented milks, and lactic acid bacteria beverages.

5. A pharmaceutical composition comprising the composition for immunostimulation according to claim 1.

6. A *Bifidobacterium* of the following (a) or (b):
   (a) *Bifidobacterium bifidum* OLB 6377 strain, Accession No. NITE BP-30, or
   (b) *Bifidobacterium bifidum* OLB 6378 strain, Accession No. NITE BP-31.

7. A method of preparing a food or drink product or a pharmaceutical composition for immunostimulation comprising incorporating the composition according to claim 1 into a food or drink product or a pharmaceutical composition.

* * * * *